US012721519B2

(12) United States Patent
Lipponen et al.

(10) Patent No.: US 12,721,519 B2
(45) Date of Patent: Sep. 1, 2026

(54) OPTICAL OPHTHALMIC APPARATUS AND METHOD OF FOCUSING IMAGE OF RETINA

(71) Applicant: OPTOMED PLC, Oulu (FI)

(72) Inventors: Juha Lipponen, Oulu (FI); Ilkka Alasaarela, Oulu (FI); Matti Pohjoisaho, Oulu (FI); Seppo Rönkkö, Oulu (FI)

(73) Assignee: OPTOMED PLC, Oulu (FI)

( * ) Notice: Subject to any disclaimer, the term of this patent is extended or adjusted under 35 U.S.C. 154(b) by 448 days.

(21) Appl. No.: 18/258,541

(22) PCT Filed: Dec. 16, 2021

(86) PCT No.: PCT/FI2021/050882

§ 371 (c)(1),
(2) Date: Jun. 20, 2023

(87) PCT Pub. No.: WO2022/136731

PCT Pub. Date: Jun. 30, 2022

(65) Prior Publication Data

US 2024/0350005 A1 Oct. 24, 2024

(30) Foreign Application Priority Data

Dec. 21, 2020 (FI) ..................................... 20206348

(51) Int. Cl.
*A61B 3/14* (2006.01)
*A61B 3/00* (2006.01)
(Continued)

(52) U.S. Cl.
CPC .............. *A61B 3/12* (2013.01); *A61B 3/0008* (2013.01); *A61B 3/0091* (2013.01); *A61B 3/103* (2013.01); *A61B 3/14* (2013.01); *A61B 3/145* (2013.01)

(58) Field of Classification Search
CPC ......... A61B 3/0025; A61B 3/113; A61B 3/12; A61B 3/0008; A61B 3/0091; A61B 3/103; A61B 3/14; A61B 3/145
(Continued)

(56) References Cited

U.S. PATENT DOCUMENTS 10,442,774 B1 * 10/2019 Krasnow .............. C07D 241/26
2016/0242644 A1 8/2016 Winsor
(Continued)

OTHER PUBLICATIONS

International Search Report and Written Opinion of the ISA for PCT/FI2021/050882 mailed Mar. 14, 2022, 12 pages.
(Continued)

*Primary Examiner* — Mahidere S Sahle
(74) *Attorney, Agent, or Firm* — Nixon & Vanderhye PC

(57) ABSTRACT

An image source of an optical ophthalmic apparatus provides a picture and directs light of the picture toward an imaging arrangement of the optical ophthalmic apparatus. The imaging arrangement receives light of the picture and forms, together with refraction of an eye, an image of the picture on a first image plane, and the imaging arrangement locates the first image plane at a known location. The imaging arrangement receives light from a retina of the eye and directs light from the retina to an image detector of the optical ophthalmic apparatus, and the imaging arrangement forms, together with refraction of the eye, an image of the retina on a second image plane. The imaging arrangement forms optical conjugates of the first and second image planes for focusing the image of the retina accurately on an image sensor of the image detector if the image of the picture is simultaneously accurately focused on the retina of the eye, and the optical ophthalmic apparatus stimulates the eye to accommodate in order to focus the image of the picture accurately on the retina if the image of the picture is out-of-focus on the retina.

15 Claims, 5 Drawing Sheets

(51) Int. Cl.
*A61B 3/103* (2006.01)
*A61B 3/12* (2006.01)

(58) Field of Classification Search
USPC ................. 351/206, 209–211, 221, 237, 243
See application file for complete search history.

(56) References Cited

U.S. PATENT DOCUMENTS

| | | | | |
|---|---|---|---|---|
| 2016/0270656 | A1* | 9/2016 | Samec | A61B 5/398 |
| 2019/0125184 | A1 | 5/2019 | Kramer et al. | |
| 2020/0029807 | A1 | 1/2020 | Jaiprakash et al. | |
| 2020/0085294 | A1 | 3/2020 | Everett et al. | |
| 2020/0196863 | A1 | 6/2020 | Anderson et al. | |
| 2020/0305711 | A1 | 10/2020 | Kramer | |

OTHER PUBLICATIONS

International Preliminary Report on Patentability for PCT/FI2021/050882 completed Jan. 12, 2023, 10 pages.
Finland Search Report for FI20206348 dated Jul. 23, 2021, 2 pages.

* cited by examiner

OPTICAL OPHTHALMIC APPARATUS AND METHOD OF FOCUSING IMAGE OF RETINA

CROSS-REFERENCE TO RELATED APPLICATIONS

This application is the U.S. national phase of International Application No. PCT/FI2021/050882 filed Dec. 16, 2021, which designated the U.S. and claims priority to FI 20206348 filed Dec. 21, 2020, the entire contents of each of which are hereby incorporated by reference.

FIELD

The invention relates to optical ophthalmic apparatus and a method of focusing an image of a retina.

BACKGROUND

Typical problem with ophthalmic instruments is how to focus the instrument to patient's eye. Namely, in order to achieve the imaging condition in sufficient accuracy, the imaging optics needs to be focused on the retina.

The problem is in general difficult with examination instruments which examine optically the portions of eye behind the iris. For example, when using a fundus camera, the fundus camera optics needs to be focused to the retina in order to capture sharp image of the retina on the camera sensor. When the ophthalmic instrument is out of focus, it leads to a blurred image and a poor image quality. An additional challenge comes from the fact that a patient is in a focused state only for short period before the eye changes its refraction/accommodation and the focus is lost.

The focusing of the existing ophthalmic instruments is made manually by the operator, or automatically by auto-focus mechanism. However, there are situations and patients where neither of the methods work well enough or are totally unusable. The operator of the ophthalmic instrument is often too slow to adjust the focus, and the patient or the eye of the patient may behave in a manner not expected by the operator. Additionally, the auto-focus is technically complicated and expensive. Hence, an improvement would be welcome.

BRIEF DESCRIPTION

The present invention seeks to provide an improvement in focusing of the optical ophthalmic apparatus.

The invention is defined by the independent claims. Embodiments are defined in the dependent claims.

LIST OF DRAWINGS

Example embodiments of the present invention are described below, by way of example only, with reference to the accompanying drawings, in which FIGS. 1A and 1B illustrate examples where the ophthalmic examination apparatus has a beam splitter for combining light to and from an eye;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

The teachings in this document relate generally to ophthalmic examination instruments, and particularly arrangements for focusing the ophthalmic examination instruments to an eye in order to examine retina of the eye.

Figure 1A:
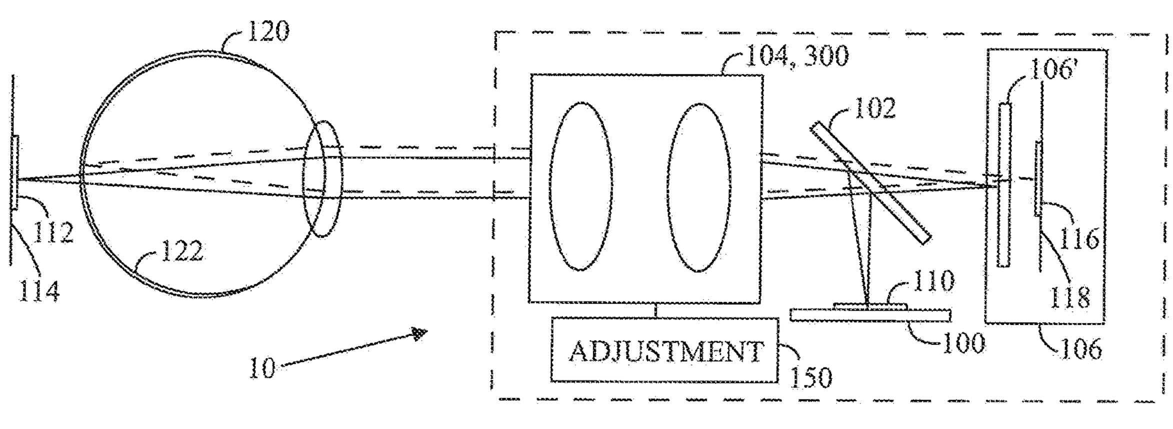
Figure 1B:
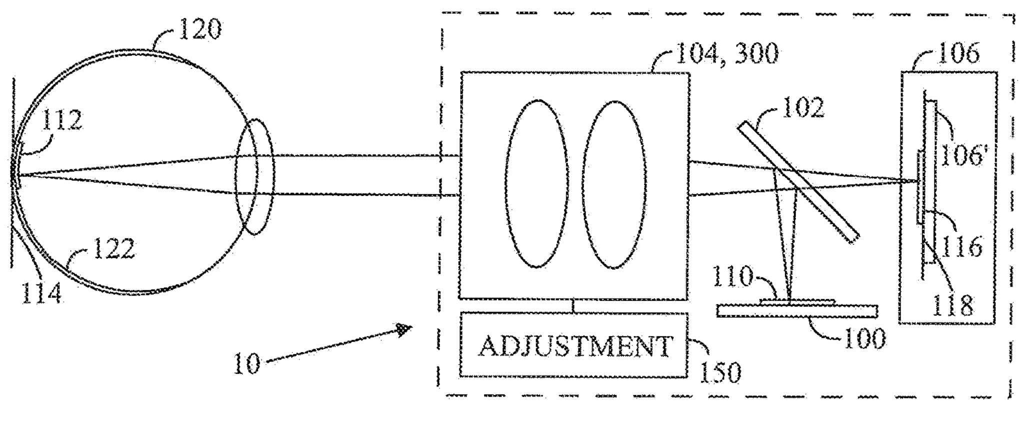
Figure 2:
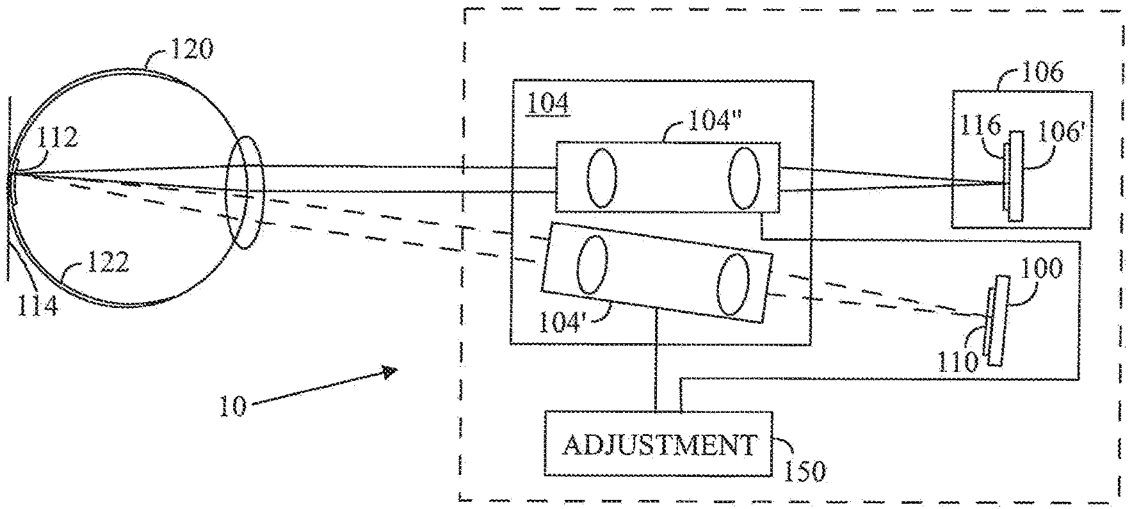
FIG. 2 illustrates an example where an imaging arrangement comprises a source imaging component and a detector side imaging component that are separate from each other.

FIGS. 1A, 1B and 2 illustrate basic examples of an optical ophthalmic apparatus 10. FIGS. 1A and 1B have a beam splitter 102, and FIG. 2 does not have the beam splitter 102. In FIG. 1A, a picture 110 is out-of-focus on a retina 122 of an eye 120. FIGS. 1B and 2 illustrate examples where the picture 110 is focused on the retina 122 of the eye 120.

An image source 100 of the optical ophthalmic apparatus 10 provides the picture 110 and directs light of the picture 110 toward an imaging arrangement 104 of the optical ophthalmic apparatus 10. The imaging arrangement 104 may comprise one of more optically refractive and/or reflective components which may form a real image or a virtual image. The one of more optically refractive and/or reflective components may comprise at least one lens and/or mirror, which has a curved surface.

The imaging arrangement 104 receives light of the picture 110 and forms, together with refraction of the eye 120, an image 112 of the picture 110 on a first image plane 114. The imaging arrangement 104 is configured to locate the first image plane 114 at a known location with respect to a typical eye of a human being when the ophthalmic apparatus 10 is at an examination position with respect to the typical eye. The examination position defines a suitable distance between the optical ophthalmic apparatus 10 and the typical eye, the suitable distance being also used when examining the eye 120. A person skilled in the art is familiar with the examination position in general. The known location of the first image plane 114 may be on a retina of the typical eye such as a standard eye model, for example. In an embodiment, the known location of the first image plane 114 may be in infinity without taking the refraction of the standard eye or the eye 120 into account. Correspondingly, the standard eye model may then be considered to be focused in infinity with the imaging arrangement 104. In an embodiment, the known location of the first image plane 114 may be at a desired distance from the optical ophthalmic apparatus 10 without taking the refraction of the standard eye or the eye 120 into account.

The typical eye may be based on an Emsley model, Emsley-Gullstrand model, or Liou and Brennan schematic eye model, for example. The eye model may be similar to an anatomical and optical eye. It may have a power of about 60.4 D and an axial length of about 24 mm for example. The eye model may estimate aberrations in a visible range of light. The eye model may have variation depending on a size of a person 160 that is examined, sex and age especially when it is a question of a child, for example. That is, a model may be selected based on anatomical and/or optical information on the person 160 to be examined.

The imaging arrangement 104 is configured to receive light from the retina 122 of the eye 120 and direct light from the retina 122 toward an image detector 106 of the optical ophthalmic apparatus 10. The imaging arrangement 104 then forms, together with refraction of the eye 120, an image 116 of the retina 122 on a second image plane 118.

The imaging arrangement 104 is configured to conjugate the first image plane 114 and the second image plane 118 to each other. That is, the first image plane 114 and the second image plane 118 are conjugate image planes. Because of the conjugation, points of the first image plane 114 are imaged into points of the second image plane 118 and (theoretically) vice versa. In this manner the image 116 of the retina 122 is accurately focused on an image sensor 106' of the image detector 106, if the image 112 of the picture 110 is simultaneously accurately focused on the retina 122 of the eye 120. If the image 112 of the picture 110 is, however, out-of-focus on the retina 122, the person 160 who is examined can see it, and the out-of-focus image 112 stimulates the eye 120 to accommodate in order to focus the image 112 of the picture 110 accurately on the retina 122. After the picture is focused accurately on the retina 122, it causes simultaneously the imaging arrangement 104 to form the second image 116 of the retina 122 in a focused manner on the image detector 106. When the retina 122 is accurately focused on an image sensor 106' a sharp image can be captured of it. The sharp image may be a still image or video.

The first image plane 114 is arranged to be an optical conjugate with the second image plane 118, which means that when the first imaging plane 114 is not at the retina 122, the retina 122 is also correspondingly out-of-focus at the image sensor 106'.

The first image plane 114 of the optical ophthalmic apparatus 10 is a surface on which the image of at least portion of the picture 110 is formed. The second image plane 118 of the optical ophthalmic apparatus 10 is a surface on which the image of at least portion of the retina 122 is formed. The image sensor 106' on which the image may be formed may be a matrix sensor such as CMOS (Complementary metal-oxide-semiconductor) or CCD (Charge Coupled Device) sensor. The image plane in general may be a reticle, a slit, a surface in a detector, a surface in a light source, or an input or output port of an optical fiber depending on the requirements and use of the ophthalmic apparatus. The image plane may be in virtual space, i.e. the image formed may be virtual instead of real image. The image plane may not be a physical object, but may be a predetermined surface in space. The image plane may locate outside the optical ophthalmic apparatus 10, and may be far away or in infinity. The image plane may not be necessarily a plane, but may be a curved surface.

The person 160 tries to focus his/her eye 120 to the picture 110. If the picture 110 is in the accommodation range of the eye 120, the person 160 may be able to bring the picture 110 to focus, after which the image of the retina 122 is also focused on the image sensor 106'.

In an embodiment, examples of which are illustrated in FIGS. 1A, 1B, 3, 4 and 5 the image source 100 directs light of the picture 110 toward the beam splitter 102 of the optical ophthalmic apparatus 10, the beam splitter 102 being configured to direct light of the picture 110 toward the eye 120. The beam splitter 102 receives light from the retina 122 of the eye 120 and directs light from the retina 122 toward the image detector 106.

Although FIGS. 1A, 1B, 3 to 5 show that light from the retina 122 passes through the beam splitter 102, it is an alternative that the image source 100 and the image detector 106 switches places and then light from the image source 100 passes through the beam splitter 102 and light from the retina 122 reflects from the beam splitter 102 to the image detector 106.

In an embodiment examples of which are shown in FIGS. 1A, 1B, 3 and 4, the imaging arrangement 104 may comprise a common optical component 300 that is common to light of the picture 110 and light received from the retina 122. [vt 3] The common optical component 300 may, for example, include one or more lenses or mirrors which participate to the image forming from the picture 110 on the first image plane 114 and from the first image plane 114 on the second image plane 118. This shared optics brings advantages such as simpler optical and mechanical structure, and in case of fundus cameras allows the instrument to have a large field-of-view.

In an embodiment an example of which is illustrated in FIG. 2, the imaging arrangement 104 may comprise a source imaging component 104' and a detector side imaging component 104" that are optically separate from each other. They may also be physically separate but they may also be structurally combined and/or integrated together. The source imaging component 104' may comprise one of more optically refractive and/or reflective components which may form a real image or a virtual image. The one of more optically refractive and/or reflective components may comprise at least one lens and/or mirror, which has a curved surface. The detector side imaging component 104" may comprise one of more optically refractive and/or reflective components which may form a real image or a virtual image. The one of more optically refractive and/or reflective components may comprise at least one lens and/or mirror, which has a curved surface.

The source imaging component 104' may receive light of the picture 110 and form, together with refraction of the eye 120, the image 112 of the picture 110 on the first image plane 114, and the source imaging component 104' may locate the first image plane 114 at the known location with respect to the typical eye of a human being.

The detector side imaging component 104" may receive light from the retina 122 of the eye 120 and direct light from the retina 122 to the image detector 106. The detector side imaging component 104" may then form, together with refraction of the eye 120, the image 116 of the retina 122 on the second image plane 118.

In this manner the image 116 of the retina 122 is accurately focused on the image sensor 106', if the image 112 of the picture 110 is simultaneously accurately focused on the retina 122 of the eye 120. If the image 112 of the picture 110 is, however, out-of-focus on the retina 122, the person 160 who is examined can see it, and the out-of-focus image 112 stimulates the eye 120 to accommodate in order to focus the image 112 of the picture 110 accurately on the retina 122. After the picture is focused accurately on the retina 122, it causes simultaneously the imaging arrangement 104 to form the second image 116 of the retina 122 in a focused manner on the image detector 106.

Figure 3:
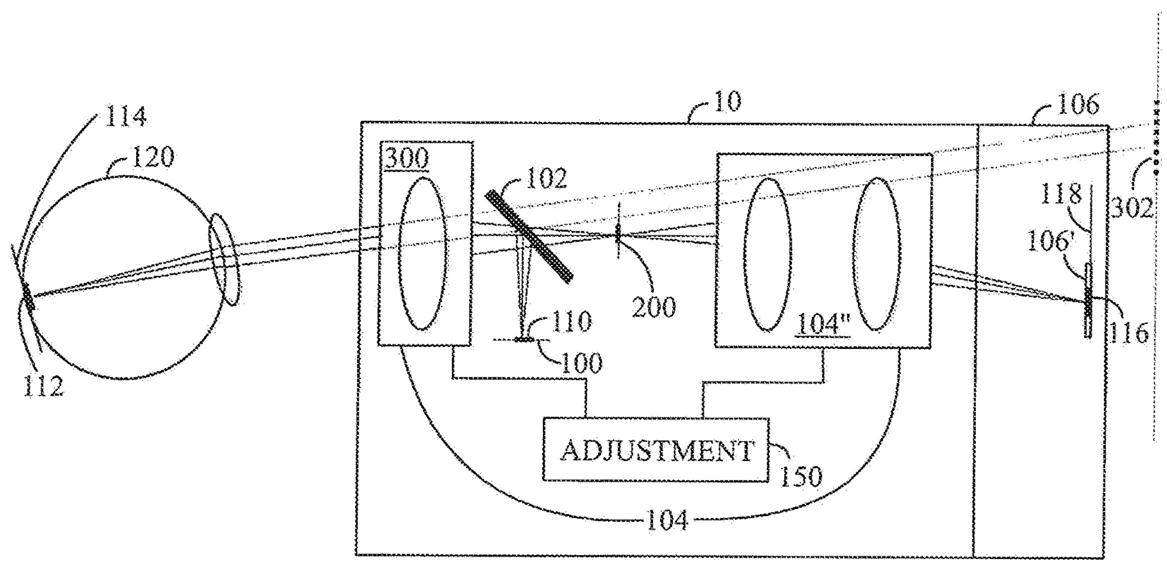
FIG. 3 illustrates an example where the ophthalmic examination apparatus forms an intermediate image of a retina.

In an embodiment an example of which is illustrated in FIG. 3, the imaging arrangement 104 may form an intermediate image 200 of the retina 122. The detector side imaging component 104" may form an image of the intermediate image 200 of the retina 122 on the second image plane 118. This kind on arrangement makes the structural and optical design easier. The intermediate image 200 may be seen by the eye 120 of the person 160 as a virtual image 302. In a case of a fundus camera, this arrangement brings advantages such as a large field-of-view, a long working distance, and a good image quality by allowing an effective aberration correction.

In an embodiment an example of which is illustrated in FIG. 4, the source imaging component 104' may form an intermediate image 250 of the picture 110. The imaging arrangement 104 may form the image 112 of the picture 110 from the intermediate image 250 of the picture 110 on the first image plane 114. This kind on arrangement gives more freedom to the structural and optical design.

This kind on arrangement gives even more freedom to the structural and optical design such as:

- a possibility to position the image source 100 further from the beamsplitter 102
- a possibility to image the picture 152 to the intermediate image 140 with a magnification other than unit magnification (larger or smaller)
- a simple implementation of external pupil for the imaging of the picture 152 to the first image plane 140 providing additional spatial guidance.

In an embodiment an example of which is illustrated in FIG. 4, the source imaging component 104' may comprise an aperture stop 400, which may be imaged to a predetermined position at front of the optical ophthalmic apparatus 10. The image 112 of the picture 110 becomes visible in the eye 120 of the person 160 when the iris of the eye 120 and the image 112 of the target aperture stop overlap at least partially. This visibility of the image 112 of the picture 110 gives additional spatial guidance to the person 160 to keep his/her eye 120 in a desired position.

In an embodiment an example of which is illustrated in FIG. 4, the detector side imaging component 104" may also comprise an aperture stop 402, which may be imaged to a predetermined position at the front of the optical ophthalmic apparatus 10. Correspondingly, the detector side imaging component 104' may comprise an aperture stop 400 which may be imaged to a predetermined position at the front of the optical ophthalmic apparatus 10. Positions of images 400', 402' of the aperture stops 400 and 402 may be precisely located in respect to eye 120 and each other so that the focusing is made through a predetermined path of the front part of the eye 120 (cornea, pupil and crystalline lens). For example, the images 400', 402' of the aperture stops 400 and 402 may coincide on the front part of the eye 120 which means that the focusing is made through the same path than the imaging by the camera lens (which refers to the detector side imaging component 104'. This means that the both focusing beam and the imaging beam are affected by the same aberrations of the eye 120, and so the focusing system is able to provide a good focus to the imaging beam.

If the person 160 is not able to focus his eye 120 to the picture 110, the optical ophthalmic apparatus 10 may comprise a focus adjustment unit 150, by which the person 160 may bring the picture 110 to the focus of his/her eye 120, and also simultaneously get retina 122 focused on the image sensor 106'.

Figure 4A:
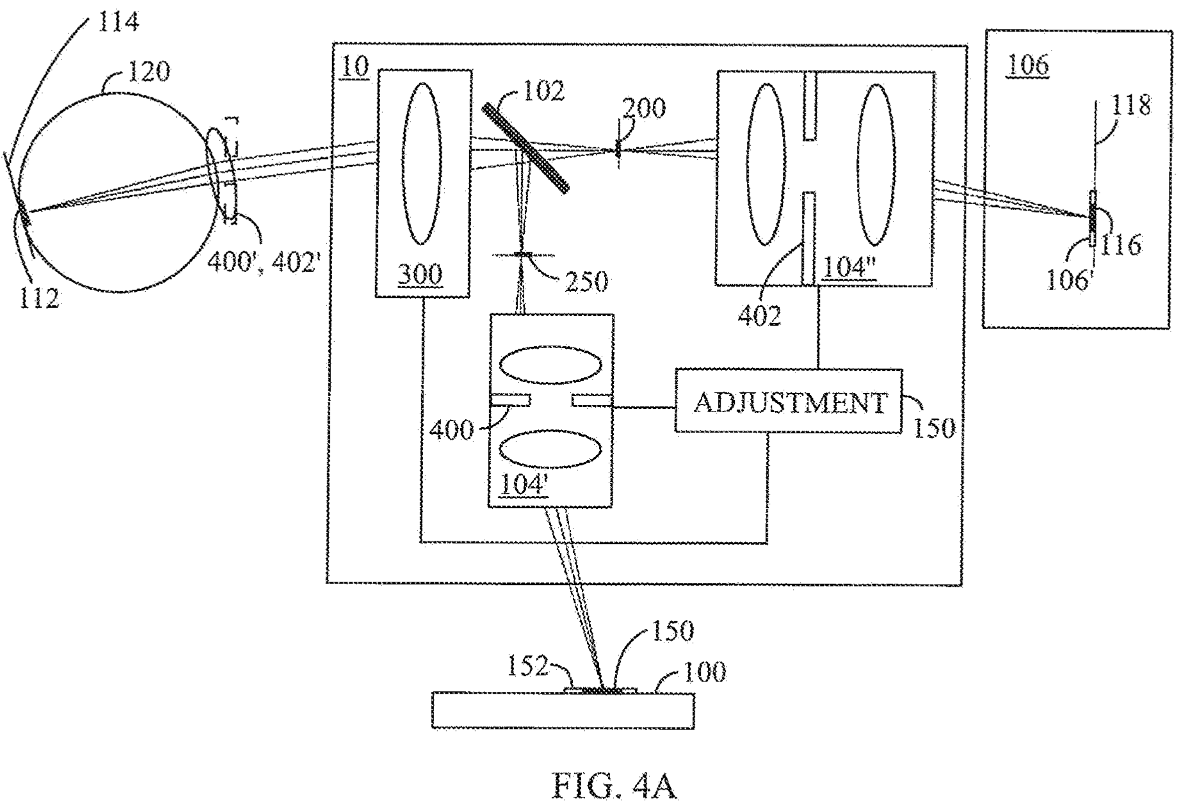
FIG. 4A illustrates an example where the ophthalmic examination apparatus forms an intermediate image of an image source.
Figure 4B:
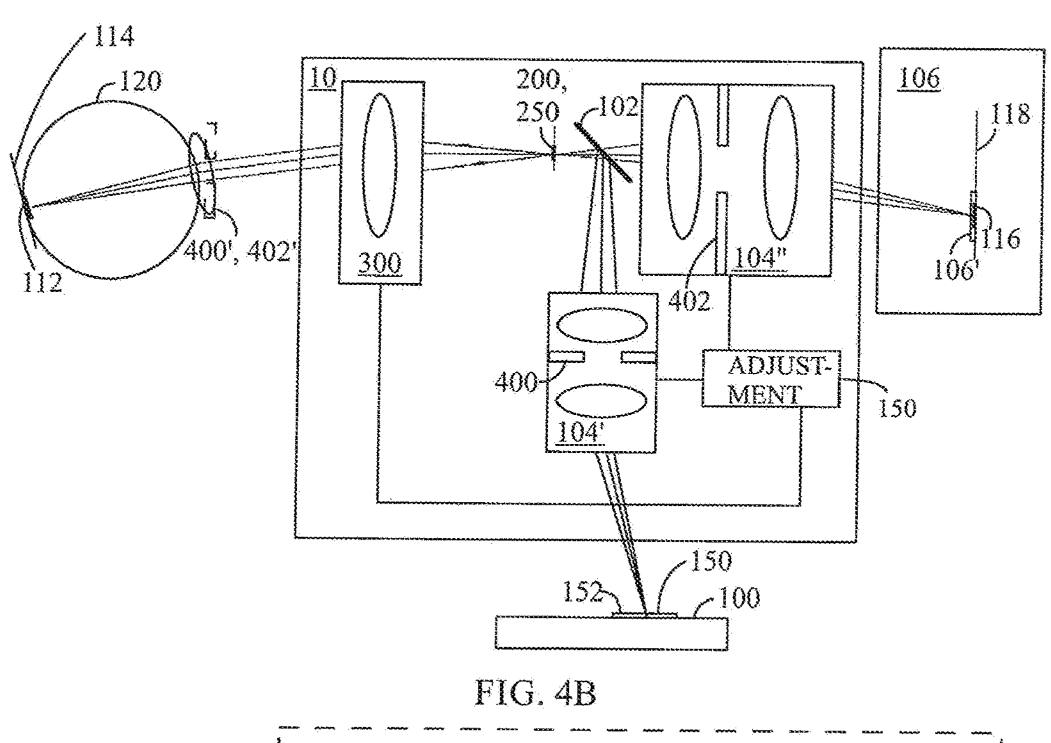
FIG. 4B illustrates another example where the ophthalmic examination apparatus forms an intermediate image of the image source.
Figure 5:
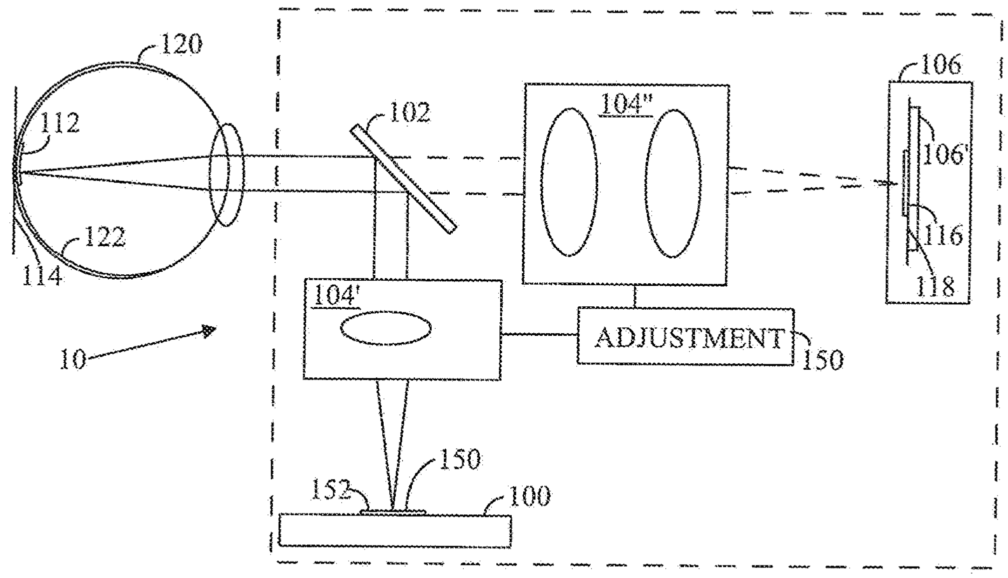
FIG. 5 illustrates an example where the ophthalmic examination apparatus has a beam splitter and separate optics for an image source and examination of the eye.
Figure 6:
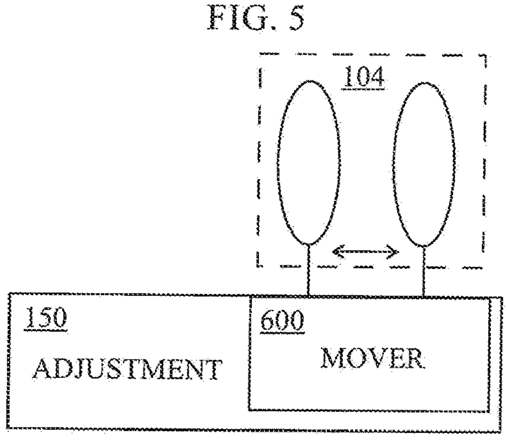
FIG. 6 illustrates an example of a mover which moves at least one lens.

FIG. 4B shows another embodiment, which is a variation of the arrangement shown in FIG. 4A. The intermediate image 200 and the intermediate image 250 are located between the common optical component 300 and the beam splitter 102.

In an embodiment examples of which are illustrated in FIGS. 1A to 5, the optical ophthalmic apparatus comprises the focus adjustment unit 150, which is configured to receive control from a person 160 the eye 120 of whom is examined and alter at least one of the following: a focal length of the imaging arrangement 104 and a distance between the imaging arrangement 104 and the first image plane 114 and/or the second image plane 118 for accurately focusing the image 112 of the picture 110 on the retina 122 of the eye 120. The person 160 whose eye 120 is examined may perform the adjustment if the image 112 of the picture 110 cannot be accurately focused on the retina 122 based on the accommodation of the eye 120.

In an embodiment, the focus adjustment unit 150 may alter at least one of the following: a focal length of the source imaging component 104' and a distance between the source imaging component 104' and the first image plane 114.

In an embodiment, the focus adjustment unit 150 may alter at least one of the following: a focal length of the detector side imaging component 104" and a distance between the detector side imaging component 104" and the second image plane 118.

In an embodiment, the focus adjustment unit 150 may alter at least one of the following: a focal length of the common optical component 300 and a distance between the common optical component 300 and the first image plane 114 and/or the second image plane 118.

The person 160 views the image of the picture 110 and adjusts his/her focus by using focus adjustment unit 150 until he/she can see the picture 110 in good sharpness. When the person 160 whose eye 120 is examined focuses the picture 110 on the retina 122, the retina 122 is simultaneously focused on the image sensor 106' of the instrument because the first and second image planes 114, 118 are arranged to be optical conjugates. The first and second image planes 114, 118 are arranged to be optical conjugates during the focusing is performed and at the moment when the focus has been achieved and maintained.

In an embodiment, the focus adjustment unit 150 may comprise a mover 600 which may be at least one of the following: a mechanical mover, an electrical mover, and a hydraulic mover, which is configured to receive the control from the person 160 and move one of more lenses of the imaging arrangement 104 with respect to each other and/or the detector 106 in order to accurately focus the image 112 of the picture 110 on the retina 122 of the eye 120. Instead of lenses the focus adjustment unit 150 may adjust a distance between a lens and a mirror, for example.

In an embodiment, the mechanical mover is configured to move in response to a force received as the control from the person 160 and convey the movement to move one of more lenses of the imaging arrangement 104 with respect to each other in order to accurately focus the first image 112 of the picture 110 on the retina 122 of the eye 120. This kind of adjustment, per se, is known to person skilled in the art. The mechanical mover may comprise a rounded control handle such as a knob, one or more cogwheels, one or more shafts and one or more conveyers or the like, for example, and the lenses are attached to the one or more conveyers such that when the person 160 turns the rounded handle, its turning movement converts into a movement of the one or more lenses of the imaging arrangement 104.

Figure 7:
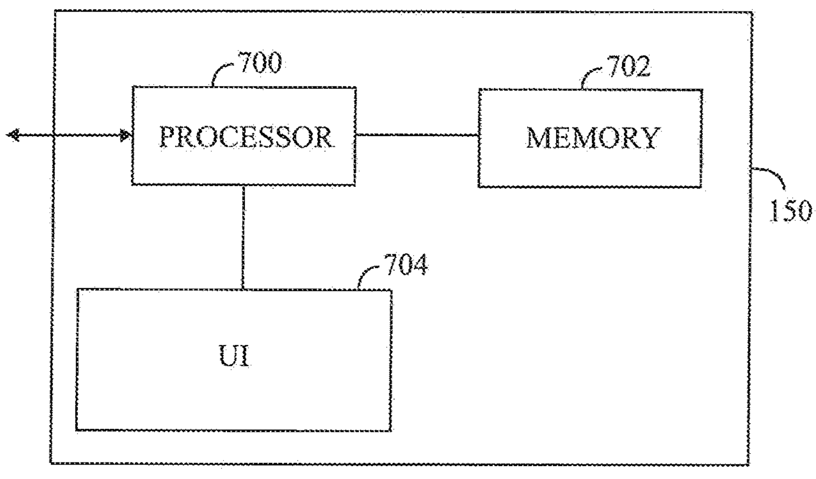
FIG. 7 illustrates an example of the adjustment unit.

In an embodiment an example of which is illustrated in FIG. 7, the focus adjustment unit 150 may comprise a user interface 704, which is configured to receive the control from the person 160, and electrically tune at least one lens of the imaging arrangement 104 or move its position with respect to at least one other lens of the imaging arrangement 104 in order to accurately focus the first image 112 on the retina 122 of the eye 120. The user interface 704 may include a screen and a keyboard and/or a touch screen, for example. The tuning of the at least one lens may be performed by electrically tuning refraction of a liquid lens, for example.

In an embodiment, the focus adjustment unit 150 comprises one or more processors 700 and one or more memories 702 including computer program code, see FIG. 7. The one or more memories 702 and the computer program code are configured to, with the one or more processors 700, cause the focus adjustment unit 150 at least to control an actuator which is configured to move one of more lenses of the imaging arrangement 104 with respect to each other in order to accurately focus the first image 112 of the picture 110 on the retina 122 of the eye 120. Alternatively or additionally, the one or more memories 702 and the computer program code are configured to, with the one or more processors 700, cause the focus adjustment unit 150 at least to control an actuator which is configured to electrically tune at least one lens of the imaging arrangement 104 in order to accurately focus the first image 112 on the retina 122 of the eye 120. The actuator may be an electrical motor which is connected with the lenses of the imaging arrangement 104 through one or more cogwheels, one or more shafts and one or more conveyers, for example.

Figure 8:
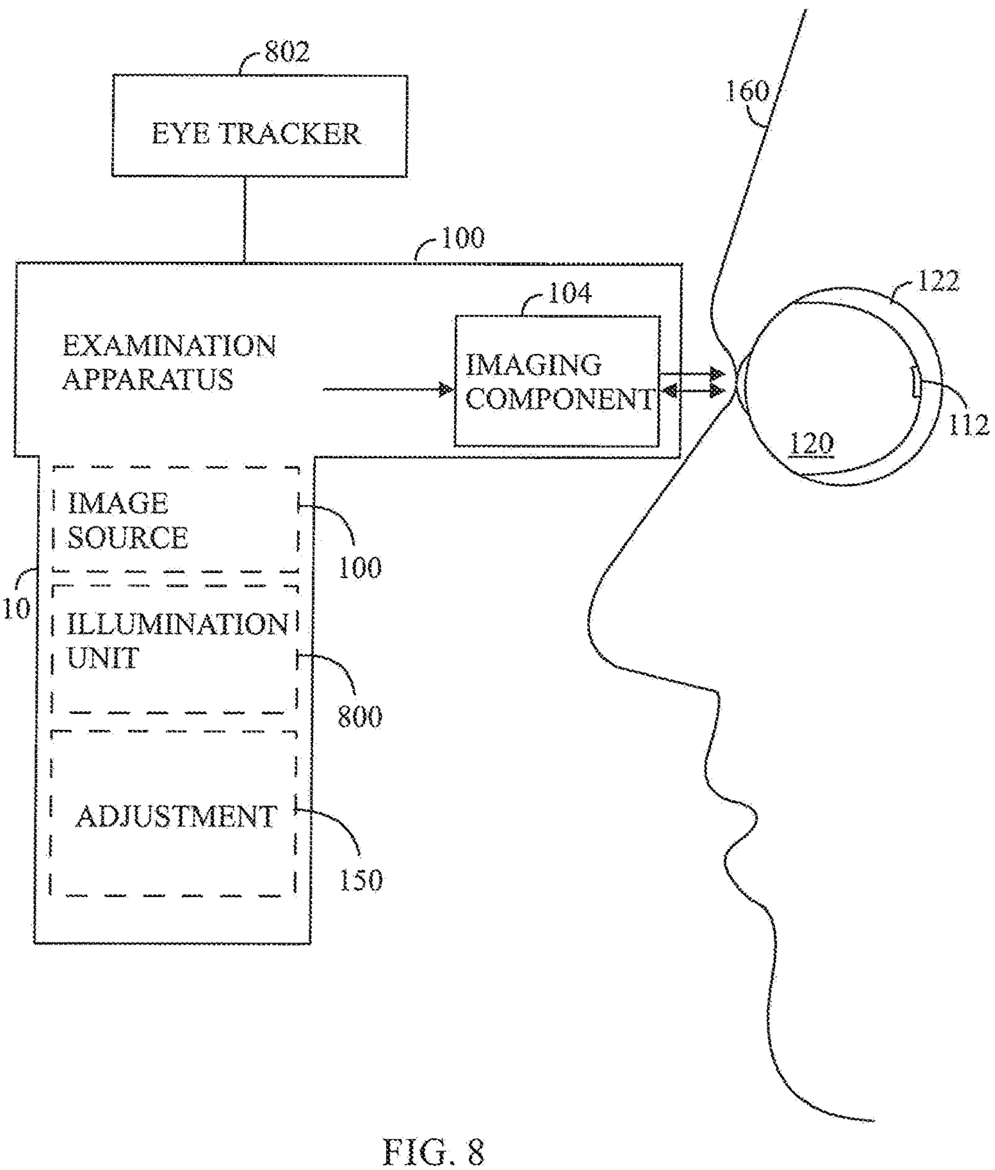
FIG. 8 illustrates an example of an ophthalmic examination apparatus in front of an eye of a patient.

FIG. 8 illustrates an example of the ophthalmic examination apparatus 10 in front of the eye 120 of a patient 160. The ophthalmic examination apparatus 10 may comprise an illumination unit 800, which illuminates the eye 120 with optical radiation which may be in the same optical band as the picture 110 or in a different optical band. The ophthalmic examination apparatus 10 may also comprise an eye tracker 802 which detects direction to which the eye 120 is gazing. The eye tracker 802 may be useful in the examination because it can indicate if the person 160 is looking in the correct direction from the examination point of view or not.

In an embodiment, the picture 110 may be arranged to locate in different angular field positions with respect to an optical axis of the optical ophthalmic apparatus 10 when viewed by the person 160. In that manner, the eye gaze direction and focus may be guided as desired for the use of the optical ophthalmic apparatus 10. For example, in fundus cameras, the picture 110 may be presented in different angular directions, and so different parts of the retina 122 may be imaged.

As the optical ophthalmic apparatus 10 or the eye 120 may have axial chromatic aberration, the picture 110 may contain light with such spectral wavelength band or spectrum, that the person 160 is guided to focus his/her eye 120 to a desired wavelength content. By presenting the picture 110 at one of the wavelengths i.e. using one narrow wavelength band, the eye can be caused to focus in a desired manner regardless the axial chromatic aberration. In an embodiment, the width of the narrow wavelength band may be about 5 nm or less, for example. In an embodiment, the width of the narrow wavelength band may be about 10 nm, for example. In an embodiment, the width of the narrow wavelength band may be about 20 nm, for example. In an embodiment, the width of the narrow wavelength band may be about 50 nm, for example. In an embodiment, the width of the narrow wavelength band may be about 100 nm, for example. In an embodiment, the width of the narrow wavelength band may be a fraction of the whole visible range.

As the eye 120 or the optical ophthalmic apparatus 10 may have astigmatism, the picture 110 may have contrast variations mainly in one dimension so that the eye 120 is guided to focus in that dimension. For example, the picture 110 may contain an array of vertical lines or vertical bars, which will guide the person 160 to find a suitable focus in horizontal dimension.

The optical ophthalmic apparatus 10 may operate in different wavelength from wavelengths of the picture 110. For example, a fundus camera may capture images of fundus by using near-infrared wavelength which is invisible or only weakly visible to the person 160. The required focus difference between the wavelengths used with the picture 110 and with the optical ophthalmic apparatus 10 may be known. Now the optical ophthalmic apparatus 10 may be arranged so, that first image plane 114 of the picture 110 and the second image plane 118 of the image of the retina 122 are optical conjugates in different wavelengths. That is, an infrared image 116 of the retina 122 is in focus when the image 112 of the picture 110 is in focus on the retina 122. The first and second image planes 114 and 118 may thus not be exact optical conjugates with the same wavelength, but they are optical conjugates such that are in focus at the same time by their corresponding wavelengths.

For example, in a fundus camera use, the picture 110 may be presented by a predetermined visible wavelength band, and the image plane position may be varied in predetermined manner when capturing images of the retina 122 by different spectral contents, such as blue, white or near-infrared bands, in order to have optimal focus with each wavelength content.

The imaging optics of the imaging arrangement 104 may comprise any optical system which, during the operation of the optical ophthalmic apparatus 10, forms an image of at least portion of the retina 122 to the second image plane 118 of the optical ophthalmic apparatus 10. The imaging optics may comprise for example lenses, mirrors, and/or diffractive optical components.

The picture 110 may be an illuminated figure, such as a dot, a cross, or a figure of any suitable shape, or an image of any suitable content, which contains features with sufficient contrast in at least one dimension, in order to provide the person 160 with an object to which he/she could try to focus his eye 120.

The picture 110 may be generated by light from one or more light sources, such as light emitting diode (LED), organic light emitting diode (OLED), incandescent bulb or laser, which are potential image sources 100, for example. The picture 110 may also be formed by a matrix of separate light sources, such as array of light emitting diodes (LED), or an organic-light-emitting display, which are also potential image sources 100. The picture 110 may also be formed by at least a partially transparent aperture or a slide, a mask, or an aperture, which may be a part of at least one light source of the image source 100. The picture 110 may be formed by using a micro-display illuminated by the light such as LCD, LCoS or OLED micro-display. The picture 110 may be formed by using a modulator which modulates the beam of light according to a figure or an image to be presented as a picture 110. The modulator may comprise an illuminated spatial or angular modulator such as liquid-crystal display (LCD), liquid-crystal on silicon (LCoS), digital micromirror device (DMD), acousto-optical modulator (AOM), scanning micro-electro-mechanical-system (MEMS), scanning mirror, or diffractive projection engine such as HOLOEYE.

The picture 110 may be formed by a micro-display which allows varying the picture according to the needs of each task performed with the instrument.

The picture 110 may be varied. In that manner, a suitable picture 110, which works well with different persons, can be used. For example, when the person 160 is a child, the used picture 100 may be different from that which works well for an adult.

Brightness, size and/or spectral content of the picture 100 may be selected and/or varied by the image source 100 in order to affect to the pupillary response of the eye 120. For example, the picture 100 may contain light mainly in red wavelengths, and the brightness of the picture 100 may be adjusted dim enough, in order not to cause the eye pupil to constrict, as it may be undesirable during the use of some ophthalmic instruments such as the fundus cameras, for example.

Although presenting the described embodiments using an examination instrument, or fundus camera, as examples, the same method may also be used with other kind or ophthalmic instruments, such as ophthalmic treatment instruments for example. This focusing method may be suitable to be used in any instrument or device which needs to be focused with the eye.

Operator may not be a person, but the instrument may be an automatic or autonomous device where the operator is replaced by automation. The operator may also not be present next to the optical ophthalmic apparatus 10, but may be in different location and operate the optical ophthalmic apparatus 10 by a remote access.

In an embodiment, the user interface 704 of the instrument may receive information on adjustment of a focus position and/or the refraction power of the instrument performed by the focus adjustment unit 150. Then the user interface 704 may output the focus position information in a numeric or electric format. The focus information may be expressed and presented as an optical power in diopters, for example. The optical power may be calibrated to correspond with the eye care lens prescription data. The eye optical power information returned by the instrument may be used to determine the focusing range of the eye, and an optimal focus position, for example.

In an embodiment, the focusing range of the eye 120 may be determined by the person the eye 120 of whom is examined, alone or together with an operator, by adjusting the focus in order to find the limits of the focus information (for example minimum and maximum of optical power in diopters) where the image 112 of the picture 110 is accurately focused on the retina 122 of the eye 120.

In an embodiment, the focusing range of the eye 120 may be determined by the operator by adjusting the focus (for example from about −20 D to about +20 D, where D denotes dioptre, without limiting to this range) and analyzing the accuracy of the image of the retina 122 on the second image plane 118. When the focus is adjusted, the eye 120 tries to accommodate in order to see the image 112 accurately. When the focus is within the focusing range of the eye 120, i.e. when the eye 120 can accommodate to get the image 112 accurately focused on the retina 122, the image of the retina 122 may at the same time be accurately focused on the second image plane 118, too. When the focus is outside the focusing range of the eye 120, i.e. when the eye 120 cannot accommodate to get the image 112 accurately focused on the retina 122, the image of the retina 122 may at the same time be out-of-focus on the second image plane 118, too. Thus, the accuracy of the image of the retina 122 on the second image plane 118 can be used to determine the limits of the accommodation range of the eye 120.

Figure 9:
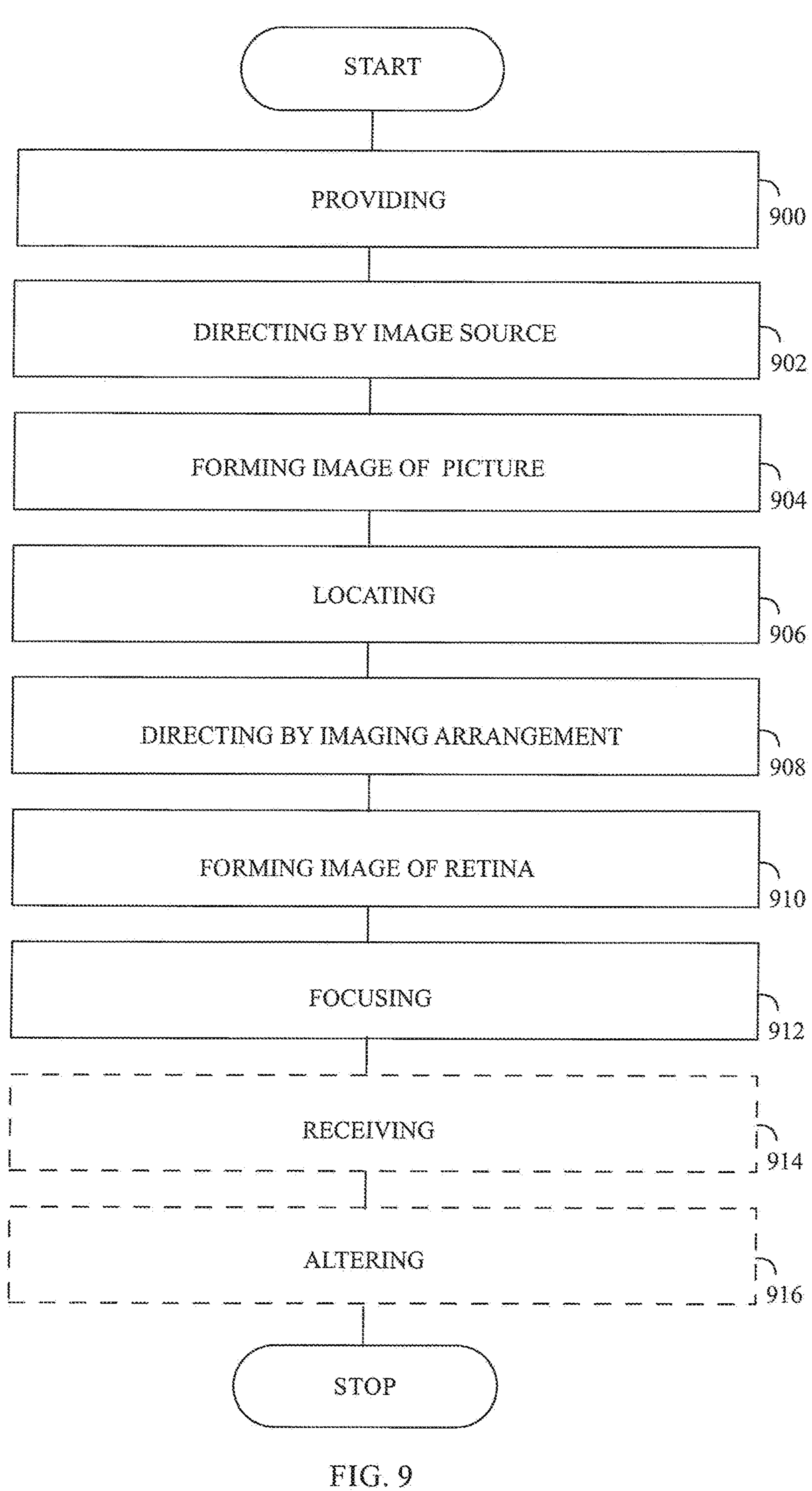
FIG. 9 illustrates of an example of a flow chart of a focusing method.

FIG. 9 is a flow chart of the measurement method. In step 900, a picture 110 is provided 900 by an image source 100 of the optical ophthalmic apparatus 10.

In step 902, light of the picture 110 is directed toward an imaging arrangement 104 of the optical ophthalmic apparatus 10 by the image source 100.

In step 904, an image 112 of the picture 110 is formed on a first image plane 114 by the imaging arrangement 104 together with refraction of an eye 120.

In step 906, the first image plane 114 is located at a known location with respect to a typical eye of a human by the imaging arrangement 104 in a situation where the optical ophthalmic apparatus 10 is in an examination position with respect to the typical eye.

In step 908, light from the retina 122 is directed to an image detector 106 of the optical ophthalmic apparatus 10 by the imaging arrangement 104.

In step 910, an image 116 of the retina 122 is formed on a second image plane 118 by the imaging arrangement 104 together with refraction of the eye 120.

In step 912, the image 116 of the retina 122 is focused accurately on an image sensor 106' of the image detector 106 by the imaging arrangement 104 the first image plane 114 and the second image plane 118 of which are optical conjugates to each other, if the image 112 of the picture 110 is simultaneously accurately focused on the retina 122 of the eye 120 by the eye 120, or the eye 120 is stimulated to accommodate in order to focus the image 112 of the picture 110 accurately on the retina 122 if the image 112 of the picture 110 is out-of-focus on the retina 122.

The next steps may be performed in an embodiment. In step 914, control is received from a person the eye 120 of whom is examined by a focus adjustment unit 150 of the optical ophthalmic apparatus 10. In step 816, at least one of the following based on the control: a focal length of the imaging arrangement 104 and a distance between the imaging arrangement 104 and the first image plane 114 or the second image plane 118 for accurately focusing the image 112 of the picture 110 on the retina 122 of the eye 120, if the image 112 of the picture 110 is out-of-focus on the retina 122 in response to the accommodation of the eye 120.

The method shown in FIG. 9 may be implemented as a logic circuit solution or computer program (see FIG. 7). The computer program may be placed on a computer program distribution means for the distribution thereof. The computer program distribution means is readable by a data processing device, and it encodes the computer program commands, carries out the measurements and optionally controls the processes on the basis of the measurements.

It will be obvious to a person skilled in the art that, as technology advances, the inventive concept can be implemented in various ways. The invention and its embodiments are not limited to the example embodiments described above but may vary within the scope of the claims.

The invention claimed is:

1. An optical ophthalmic apparatus, comprising:

an imaging arrangement; and an image source configured to provide a picture and direct light of the picture toward the imaging arrangement of the optical ophthalmic apparatus; wherein:

the imaging arrangement is configured to receive light of the picture and form, together with refraction of an eye, an image of the picture on a first image plane, and the imaging arrangement is configured to locate the first image plane at a known location, the imaging arrangement is configured to receive light from a retina of the eye and direct light from the retina to an image detector of the optical ophthalmic apparatus, and the imaging arrangement is configured to form, together with refraction of the eye, an image of the retina on a second image plane;

the imaging arrangement is configured to form optical conjugates of the first image plane and the second image plane for focusing the image of the retina accurately on an image sensor of the image detector if the image of the picture is simultaneously accurately focused on the retina of the eye, and the optical ophthalmic apparatus is configured to stimulate the eye to accommodate in order to focus the image of the picture accurately on the retina if the image of the picture is out-of-focus on the retina; and the optical ophthalmic apparatus comprises a focus adjustment unit, which is configured to receive control from a person the eye of whom is examined and alter at least one of the following: a focal length of the imaging arrangement and a distance between the imaging arrangement and the first image plane or the second image plane for accurately focusing the image of the picture on the retina of the eye based on the control, if the image of the picture is out-of-focus on the retina based on the accommodation of the eye, wherein the imaging arrangement comprises a common optical component that is common to light of the picture and light received from the retina, and wherein the focus adjustment unit is configured to modify at least the common optical component.

2. The optical ophthalmic apparatus of claim 1, wherein the image source is configured direct light of the picture toward a beam splitter of the optical ophthalmic apparatus, the beam splitter being configured to direct light of the picture toward the eye; and the beam splitter is configured to receive light from a retina of the eye and direct light from the retina toward the image detector.

3. The optical ophthalmic apparatus of claim 1, wherein the imaging arrangement comprises a source imaging component and a detector side imaging component that are separate from each other;

the source imaging component is configured to receive light of the picture and form, together with refraction of an eye, the image of the picture on the first image plane, and the source imaging component is configured to locate the first image plane at the known location with respect to the typical eye of a human being in response to the examination position between the optical ophthalmic apparatus and the eye; and the detector side imaging component is configured to receive light from the retina of the eye and direct light from the retina to the image detector, and the detector side imaging component is configured to form, together with refraction of the eye, the image of the retina on the second image plane.

4. The optical ophthalmic apparatus of claim 3, wherein the imaging arrangement is configured to form an intermediate image of the retina, and the detector side imaging component is configured to form an image of the intermediate image of the retina on the second image plane.

5. The optical ophthalmic apparatus of claim 3, wherein the source imaging component is configured to form an intermediate image of the picture, and the imaging arrangement is configured to form the image of the picture from the intermediate image of the picture on a first image plane.

6. The optical ophthalmic apparatus of claim 1, wherein the focus adjustment unit comprises a mover that comprises at least one of the following: a mechanical mover, an electrical mover, and a hydraulic mover, the mover being configured to receive the control from the person and move one of more lenses of the imaging arrangement with respect to each other and/or the detector in order to accurately focus the image of the picture on the retina of the eye.

7. The optical ophthalmic apparatus of claim 6, wherein the mover is a mechanical mover that is configured to move in response to a force received as the control from the person and convey the movement to move one of more lenses of the imaging arrangement with respect to each other in order to accurately focus the first image of the picture on the retina of the eye.

8. The optical ophthalmic apparatus of claim 1, wherein the focus adjustment unit comprises a user interface, which is configured to receive the control from the person and electrically tune at least one lens of the imaging arrangement in order to accurately focus the first image on the retina of the eye.

9. The optical ophthalmic apparatus of claim 8, wherein the user interface is configured to receive information on adjustment of a focus position and/or a refraction power performed by the focus adjustment unit, and output the focus position information in a numeric or electric format.

10. The optical ophthalmic apparatus of claim 1, wherein the first image plane and the second image plane are optical conjugates in different wavelengths.

11. The optical ophthalmic apparatus of claim 8, wherein the image source comprises a modulator, which is configured to form the picture.

12. A method of focusing an image of a retina of an eye on an image sensor of the image detector of optical ophthalmic apparatus, the method comprising providing, by an image source of the optical ophthalmic apparatus, a picture;

directing, by the image source, light of the picture toward an imaging arrangement of the optical ophthalmic apparatus, the method comprising forming, by the imaging arrangement together with refraction of an eye, an image of the picture on a first image plane;

locating, by the imaging arrangement, the first image plane at a known location with respect to a typical eye of a human being in a situation where the optical ophthalmic apparatus is in an examination position with respect to the typical eye;

directing, by the imaging arrangement, light from the retina to an image detector of the optical ophthalmic apparatus;

forming, by the imaging arrangement together with refraction of the eye, an image of the retina on a second image plane;

focusing, by the imaging arrangement the first image plane and the second image plane of which are optical conjugates to each other, the image of the retina accurately on an image sensor of the image detector if the image of the picture is simultaneously accurately focused on the retina of the eye by the eye, or stimulating the eye to accommodate in order to focus the image of the picture accurately on the retina if the image of the picture is out-of-focus on the retina; and receiving, by a focus adjustment unit of the optical ophthalmic apparatus, control from a person the eye of whom is examined and altering at least one of the following: a focal length of the imaging arrangement and a distance between the imaging arrangement and the first image plane or the second image plane for accurately focusing the image of the picture on the retina of the eye based on the control, if the image of the picture is out-of-focus on the retina based on the accommodation of the eye, wherein the imaging arrangement comprises a common optical component that is common to light of the picture and light received from the retina, and wherein the focus adjustment unit is configured to modify at least the common optical component.

13. The method of claim 12, further comprising receiving, by the focus adjustment unit of the optical ophthalmic apparatus, control from a person the eye of whom is examined; and altering at least one of the following based on the control: a focal length of the imaging arrangement and a distance between the imaging arrangement and the first image plane or the second image plane for accurately focusing the image of the picture on the retina of the eye, if the image of the picture is out-of-focus on the retina in response to the accommodation of the eye.

14. The optical ophthalmic apparatus of claim 1, wherein the focus adjustment unit is configured to modify at least the common optical component to alter the focal length of the imaging arrangement and/or the distance between the imaging arrangement and the first image plane or the second image plane.

15. A method of focusing an image of a retina of an eye on an image sensor of the image detector of optical ophthalmic apparatus, the method comprising providing, by an image source of the optical ophthalmic apparatus, a picture;

directing, by the image source, light of the picture toward an imaging arrangement of the optical ophthalmic apparatus, the method comprising forming, by the imaging arrangement together with refraction of an eye, an image of the picture on a first image plane;

locating, by the imaging arrangement, the first image plane at a known location with respect to a typical eye of a human being in a situation where the optical ophthalmic apparatus is in an examination position with respect to the typical eye;

directing, by the imaging arrangement, light from the retina to an image detector of the optical ophthalmic apparatus;

forming, by the imaging arrangement together with refraction of the eye, an image of the retina on a second image plane;

focusing, by the imaging arrangement the first image plane and the second image plane of which are optical conjugates to each other, the image of the retina accurately on an image sensor of the image detector if the image of the picture is simultaneously accurately focused on the retina of the eye by the eye, or stimulating the eye to accommodate in order to focus the image of the picture accurately on the retina if the image of the picture is out-of-focus on the retina; and receiving, by a focus adjustment unit of the optical ophthalmic apparatus, control from a person the eye of whom is examined and altering at least one of the following: a focal length of the imaging arrangement and a distance between the imaging arrangement and the first image plane or the second image plane for accurately focusing the image of the picture on the retina of the eye based on the control, if the image of the picture is out-of-focus on the retina based on the accommodation of the eye, wherein the imaging arrangement comprises a common optical component that is common to light of the picture and light received from the retina, and wherein the focus adjustment unit is configured to modify at least the common optical component to alter the focal length of the imaging arrangement and/or the distance between the imaging arrangement and the first image plane or the second image plane.

* * * * *